United States Patent [19]

Kasat et al.

[11] Patent Number: 5,424,070
[45] Date of Patent: Jun. 13, 1995

[54] TRANSPARENT CLEAR STICK COMPOSITION

[75] Inventors: Radhakrishna B. Kasat, Belle Mead; Bhalchandra D. Moghe, Edison, both of N.J.

[73] Assignee: The Mennen Company, Morristown, N.J.

[21] Appl. No.: 54,300

[22] Filed: Apr. 30, 1993

[51] Int. Cl.$^6$ .................. A61K 7/32; A61K 47/00
[52] U.S. Cl. .................... 424/401; 424/65; 424/DIG. 5; 514/772; 514/784; 514/844
[58] Field of Search ............ 424/65, DIG. 5, 401; 514/772, 784, 844

[56] References Cited

U.S. PATENT DOCUMENTS

| | | | |
|---|---|---|---|
| 3,444,091 | 5/1969 | Petraglia | 252/315.4 |
| 4,154,816 | 5/1979 | Roehl et al. | 424/68 |
| 4,268,498 | 5/1981 | Gedeon et al. | 424/59 |
| 4,759,924 | 7/1988 | Luebbe et al. | 424/42 |
| 4,904,466 | 2/1990 | Carson et al. | 424/83 |
| 4,948,578 | 8/1990 | Burger et al. | 424/68 |
| 4,980,078 | 12/1990 | Verite et al. | 252/118 |
| 5,114,717 | 5/1992 | Kuznitz et al. | 424/401 |
| 5,120,541 | 6/1992 | Macaulay et al. | 424/401 |
| 5,128,123 | 7/1992 | Brewster et al. | 424/65 |
| 5,221,529 | 6/1993 | Tansley | 424/DIG. 5 |

FOREIGN PATENT DOCUMENTS

0450597A2  4/1991  European Pat. Off. .

*Primary Examiner*—Raymond J. Henley, III
*Attorney, Agent, or Firm*—Antonelli, Terry, Stout & Kraus

[57] ABSTRACT

Disclosed is a clear, transparent cosmetic solid stick composition containing an alcohol such as propylene glycol, and water, and gelled with a soap such as sodium stearate. The composition also includes an Eumulgin compound, such as Eumulgin L (PPG-2-Ceteareth-9), to provide the solid cosmetic stick composition with clarity and transparency, which clarity and transparency is maintained over an extended period of time. The composition can also include both sodium chloride and stearyl alcohol, to increase the melting point of the composition. Deodorant active materials can be included in the composition to provide clear, transparent deodorant solid sticks.

35 Claims, No Drawings

TRANSPARENT CLEAR STICK COMPOSITION

BACKGROUND OF THE INVENTION

The present invention relates to cosmetic stick compositions, in particular, cosmetic solid stick compositions, such as deodorant solid stick compositions. More specifically, the present invention relates to a deodorant solid stick composition containing a base of an alcohol (for example, a monohydric alcohol, such as ethanol, or a polyhydric alcohol, such as propylene glycol), together with water, gelled with a soap (for example, an alkali metal salt of a saturated fatty acid). In particular, the present invention relates to a transparent, clear cosmetic (deodorant) solid stick composition with improved clarity and transparency, thereby achieving an improved appearance, retaining such improved clarity and transparency over an extended period of time.

It has been desired to provide a soap-gelled, transparent clear cosmetic stick composition, such as a soap-gelled transparent clear deodorant solid stick composition, which retains transparency and clarity over an extended period of time so as to have a long shelf life. It has also been desired to provide such a transparent stick composition, having a long shelf life, which avoids crystals forming in the stick, and which has a high melting point. Such high melting point can facilitate production of the packaged stick composition, since the packaged stick composition can harden faster; moreover, due to the high melting point, storage and shipment of the packaged product is facilitated.

U.S. Pat. No. 4,759,924, the contents of which are incorporated herein by reference in their entirety, discloses transparent, soap-gelled cosmetic stick compositions including a polyhydric aliphatic alcohol containing 2 to 6 carbon atoms; water; a soap gel-forming agent; and a hydro-alcoholic soluble emollient, having the formula $R(OC_3H_6)_a(OC_2H_4)_bOH$, where R is either hydrogen or a hydrocarbon chain having from about 1 to 18 carbon atoms, and $a/(a+b) \leq 0.5$. This patent discloses that the polyhydric alcohol can illustratively be ethylene glycol or propylene glycol, and that mixtures of polyols can be used; and that illustratively the gel-forming agent can be the sodium, potassium and aluminum salts of fatty acids containing from about 14 to 18 carbon atoms. Preferred fatty acid soap gel-forming agents include sodium stearate, sodium palmitate, potassium stearate, potassium palmitate, sodium myristate and aluminum monostearate. Illustrative hydro-alcoholic soluble emollients include PPG-5-Ceteth 20, PPG-3-Myreth-3, PEG-20-Laurate, PEG-6-32 and Polyoxamer 335.

U.S. Pat. No. 4,759,924 further discloses that the stick composition can include various optional ingredients, including conventional deodorant materials; and that the stick composition (e.g., gel stick) can be used by the consumer by rubbing the stick on the area of the body where application is desired. For example, in the case of a deodorant stick, the stick is rubbed in the axillary area to apply the deodorant agent.

While U.S. Pat. No. 4,759,924 describes a stick composition that it indicates to be transparent, this patent does not disclose that transparency of the stick composition can be maintained over an extended period of time.

U.S. Pat. No. 5,114,717 discloses a clear gel stick composition including a polyhydric alcohol and a soap, and further including an alkoxylate copolymer; the composition further includes fragrancing compounds, with the fragrancing compounds in the composition including from at most 25%, 0.1%, total ester compounds by weight of the fragrance. This patent discloses that the alkoxylate copolymer has the formula $R_f[(C_2H_4O)_a(C_3H_6O)_b(C_2H_4O)_c(C_3H_6O)_d]_e[H]_g$, wherein R is selected from the group consisting of hydrogen, a $C_{10}$–$C_{22}$ fatty alkoxide chain, ethylene-diamine, and combinations thereof; a, b, c and d are independently selected integers ranging from 0 to 200 with a proviso that the sum of a, b, c and d is at least 5; e is an integer from 1 to 4; f is an integer from 0 to 1; and g is an integer from 0 to 4. This patent is based upon a discovery that certain types of fragrance components adversely effect clarity of soap-based cosmetic sticks, and that the fragrance components must be controlled for maintenance of stick clarity.

U.S. Pat. No. 5,128,123 discloses cosmetic compositions, in the form of sticks, which are clear and mild, containing (in addition to a polyhydric alcohol having from 2 to 6 carbon atoms and from 2 to 6 hydroxyl groups, water, and a soap) an alkoxylate copolymer, and a clarifying agent (which is a basic amine) present in an effective amount to maintain clarity of the stick. The alkoxylate copolymer has a formula $[A-CH_2CH_2-A]_f[(C_2H_4O)_a(C_3H_6O)_b(C_2H_4O)_c(C_3H_6O)_d]_e[H]_g$, wherein A is nitrogen; a, b, c and d are independently selected integers ranging from 0 to 200 with the proviso that the sum of a, b, c and d is at least about 50; e is an integer from 1 to 4; f is an integer from 0 to 1; and g is an integer from 0 to 4. This patent discloses that the copolymer partially replaces the soap as a structurant in the stick. This patent further discloses that when f and e are 0 and 1, respectively, the structure described is a poly(ethylene oxide)(propylene oxide)(ethylene oxide) copolymer. This patent further discloses that the clarifying agent is preferably selected from amino alkanols having from 2 to 6 hydroxyl groups, particularly effective being the propanol amines.

U.S. Pat. No. 5,128,123 also defines what is meant by the term "clear" with respect to the stick composition described therein. Specifically, the term "clear" has its usual dictionary definition; thus, a clear cosmetic stick, like glass, allows for ready viewing of objects behind it. This patent contrasts clear cosmetic sticks with translucent cosmetic sticks, which allow light to pass through but causes the light to be so scattered that it will be impossible to clearly identify objects behind the translucent stick. This patent then goes on to define clear, translucent and opaque sticks based on transmittance of light of wavelength in the range of 400 to 900 nm through a sample 1 cm thick. These definitions with respect to clear, translucent and opaque are also appropriate for the present invention. In addition, according to the present invention the term "transparent" is given its usual dictionary definition; that is, having the property of transmitting light therethrough so that bodies behind can be distinctly seen.

U.S. Pat. No. 4,268,498, the contents of which are incorporated herein by reference in their entirety, discloses a substantially clear cosmetic stick in which there are incorporated high levels of cosmetically active ingredients, the substantially clear cosmetic stick being non-irritating to the skin. The stick contains, as essential ingredients, polyoxyethylene (17–23)-glucose-fatty acid ester, polyoxyethylene (20–26) ether of a long-chain alcohol, polyoxypropylene (2–5) ether of a long-chain alcohol, sodium salt of a fatty acid, propylene glycol, lower alkyl ester of fatty acids, water, and a cosmetically active ingredient. This patent discloses that the cosmetically active ingredients include fragrances, sunscreens, skin conditioners, nail conditioners, deodorants and the like.

U.S. Pat. No. 5,120,541 discloses a transparent cosmetic stick composition having a lamellar structure and including an alcohol and soap, and optionally water, and further including a soap crystal growth inhibitor. This soap crystal growth inhibitor inhibits growth of soap crystals in the composition so as to achieve improved transparency, even in stick compositions containing relatively large amounts of monohydric alcohol. The soap crystal growth inhibitors include substituted or unsubstituted short-chain nonionics (a carbon chain length of less than $C_{24}$).

European Patent Application No. 450,597A2 discloses another transparent cosmetic gel stick composition. This composition consists essentially of an aliphatic polyhydric alcohol (such as propylene glycol); a soap (such as sodium stearate); a water-soluble emollient selected from the group consisting of (1) polyoxyethylene ethers of fatty alcohols, (2) polyoxyethylene-/polyoxypropylene ethers of fatty alcohols, and (3) polyoxyethylene glycols; and water, the composition further including a water-dispersible emollient that is a polyoxyethylene ether of a branched chain fatty alcohol. This European patent document discloses that incorporation of the water-dispersible emollient in the composition including the polyhydric alcohol, soap, water and water-soluble emollient provides a gel solid stick composition that has better transparency to transmission of light as compared to the same composition not containing the water-dispersible emollient.

U.S. Pat. No. 4,154,816 discloses a transparent antiperspirant solid stick composition containing an antiperspirant metal compound, lower monohydric alcohols (such as ethanol and isopropanol), di- and/or trihydric alcohols (such as propylene glycol and/or lower polyglycols), propylene-/ethyleneglycol-polycondensate, dibenzaldehyde-mono-sorbitol acetal as a gelling agent, and mono-or dialkylol-amides of higher fatty acids. The propylene-/ethylene glycol-polycondensate has the formula $HO(C_2H_4O)_x(C_3H_6O)_yH$, where $y/(x+y)$ is from 0.6 to 1, and has an average molecular weight of at least 500. The composition of this patent uses an acetal, and not a soap, as the gelling agent; and contains, e.g., an acidic reacting antiperspirant compound, which causes decomposition of the soap.

As seen in the foregoing, various solid stick (e.g., deodorant) compositions, including compositions stated to be transparent, are known. However, it is still desired to provide solid stick compositions including an alcohol and gelled with a soap, which are clear and transparent, and retain their clarity and transparency for relatively long periods of time. Moreover, it is still desired to provide such solid stick compositions, having various cosmetic active ingredients (such as deodorant active ingredients) incorporated therein, that have such clarity and transparency and maintain such clarity and transparency, and which have a high melting point.

SUMMARY OF THE INVENTION

Accordingly, it is an object of the present invention to provide a cosmetic stick composition (e.g., a cosmetic solid stick composition) that is clear and transparent, and that is compatible (has such clarity and transparency) when cosmetic active ingredients are incorporated therein.

It is a further object of the present invention to provide a cosmetic solid stick composition that is clear and transparent when including deodorant active materials, such as conventional deodorant active materials, in the stick composition.

It is a further object of the present invention to provide a transparent, clear stick-composition (including transparent, clear deodorant stick compositions), which maintains clarity and transparency for relatively long periods of time.

It is a further object of the present invention to provide a transparent, clear cosmetic stick composition containing alcohol and water, and gelled by a soap (such as alkali metal salts of fatty acids), which maintains clarity and transparency for long periods of time.

It is a still further object of the present invention to provide a transparent, clear cosmetic solid stick composition, including deodorant solid stick compositions, having a high melting point.

The above objects are achieved, according to the present invention, by incorporating Eumulgin compounds in a stick composition containing alcohol (e.g., polyhydric alcohol) and water and galled with a soap (e.g., sodium salts of fatty acids having carbon chain length $C_{12}-C_{22}$). The Eumulgin compounds are contained in the stick composition in an effective amount to provide clarity and transparency to the stick composition, and maintain such clarity and transparency. Illustratively, and not to limit the present invention, the above objectives are achieved by incorporating, in a cosmetic stick composition containing propylene glycol and water and gelled with sodium salts of fatty acids of $C_{12}-C_{22}$ carbon chain length, a polyoxypropylene-polyoxyethylene ether of cetearyl alcohol having the CTFA (Cosmetics, Toiletry and Fragrance Association, Inc.) designation: PPG-2-Ceteareth-9; this incorporated material is available under the name Eumulgin L (Henkel).

Other Eumulgin compounds than Eumulgin L, such as Eumulgin B-3, can be incorporated in the composition containing, e.g., propylene glycol and water and gelled with the soap, to achieve the objectives according to the present invention of a clear, transparent cosmetic solid stick composition.

The Eumulgin compounds are a series of compounds as described in the *CTFA International Cosmetic Ingredient Dictionary* (4th Edition 1991), the contents of which are enclosed herewith by reference in their entirety. Various of the Eumulgin compounds are set forth in the following, with their CTFA adopted name set forth parenthetically: Eumulgin 286 (Nonoxynol-10); Eumulgin B-1 (Ceteareth-12); Eumulgin B-2 (Ceteareth-20); Eumulgin B-3 (Ceteareth-30); Eumulgin C4(PEG-5 Cocamide); Eumulgin HRE 40 (PEG-40 Hydrogenated Castor Oil); Eumulgin HRE 60 (PEG-60 Hydrogenated Castor Oil); Eumulgin L (PPG-2-Ceteareth-9); Eumulgin M8 (Oleth-10 and Oleth-5); Eumulgin O5 (Oleth-5); Eumulgin O10 (Oleth-10); Eumulgin RO40 (PEG-40 Castor Oil); Eumulgin SML 20 (Polysorbate 20); Eumulgin SMO 20 (Polysorbate 80); Eumulgin SMS 20 (Polysorbate 60); and Eumulgin ST8 (PEG-8 Stearate). By use of the term "Eumulgin compounds" in this disclosure, we mean the compounds designated as Eumulgin compounds in the *CTFA International Cosmetic Ingredient Dictionary* (4th Edition 1991) and set forth in the foregoing.

Preferably, the amount of Eumulgin compound (e.g., Eumulgin L) incorporated in the stick composition is 1-9% by weight Eumulgin compound per total weight of the composition, in order to achieve the most satisfactory transparency and clarity of the stick composition.

The above objectives are further achieved by incorporating sodium chloride and stearyl alcohol in the composition containing the alcohol and water and gelled with the soap, and also containing the Eumulgin compound. The sodium chloride and stearyl alcohol act to increase the melting point of the composition, causing the stick to solidify at a higher temperature which facilitates the manufacturing process. Furthermore, by providing the stick composition having a higher melting point, the product can be stored at (or subjected to) higher temperatures without melting, facilitating storage and transportation of the product.

Preferably, the sodium chloride can be incorporated in the composition in an amount up to 1% by weight of the total weight of the composition, while the stearyl alcohol can be incorporated in the composition in an amount up to 0.5% by weight of the total weight of the composition.

Accordingly, by the present invention, which incorporates an Eumulgin compound in the soap-gelled solid stick composition containing an alcohol and water, a solid stick composition is provided that is transparent and clear, and retains its clarity and transparency over relatively long periods of time. Moreover, by incorporating the sodium chloride and stearyl alcohol in the composition, a stick composition having a relatively high melting point is achieved.

DETAILED DESCRIPTION OF THE INVENTION

While the invention will be described in connection with specific and preferred embodiments, it will be understood that it is not intended to limit the invention to those embodiments. To the contrary, it is intended to cover all alterations, modifications and equivalents as may be included within the spirit and scope of the invention as defined by the appended claims.

Throughout the present specification, where compositions are described as including or comprising specific components, it is contemplated by the inventors that compositions of the present invention also consist essentially of, or consist of, the recited components. Accordingly, throughout the present disclosure any described composition can consist essentially of, or consist of, the recited components.

The present invention contemplates a clear and transparent cosmetic stick composition (in particular, a clear and transparent cosmetic solid stick composition, such as clear and transparent deodorant solid stick compositions) containing alcohol and water, and gelled with alkali metal salts of fatty acids (that is, the composition further containing alkali metal salts of fatty acids as gelling agents, for the alcohol and water), the composition further including at least one Eumulgin compound. A preferred Eumulgin compound is Eumulgin L (CTFA name: PPG-2-Ceteareth-9). The incorporation of the Eumulgin compound in the composition improves clarity and transparency of the composition and helps retain the clarity and transparency of the composition over extended periods of time.

The present invention also contemplates a clear and transparent cosmetic stick composition containing water and an alcohol, and gelled with a soap, having the Eumulgin compound therein, and further including both sodium chloride and stearyl alcohol. By incorporating the sodium chloride and stearyl alcohol in the composition, melting point of the composition is raised as compared with the melting point of the same composition without the sodium chloride and stearyl alcohol.

Incorporation of both sodium chloride and stearyl alcohol in various soap-gelled cosmetic stick compositions has previously been described in U.S. patent application Ser. No. 07/725,677, filed Jul. 3, 1991, the contents of which are incorporated herein by reference in their entirety. By incorporating the sodium chloride and stearyl alcohol in the composition according to this aspect of the present invention, achieving a high melting point composition, production of the composition, packaged as a solidified product in a container, is facilitated, and a melting of the packaged product during storage or transportation can easily be avoided.

The alcohol incorporated in the solid stick composition of the present invention can be a monohydric alcohol and/or polyhydric alcohol (for example, ethanol as a monohydric alcohol, and propylene glycol and dipropylene glycol as polyhydric alcohol). The alcohol can be a mixture of alcohols, including a mixture of monohydric and polyhydric alcohols or a mixture of monohydric alcohols or a mixture of polyhydric alcohols. Various polyhydric alcohols which can be used in soap-gelled alcohol-and water-containing sticks are described in U.S. Pat. No. 4,759,924, the contents of which have previously been incorporated herein by reference in their entirety, and can also be used in the present invention.

In addition, mixtures of alcohols can be utilized according to the present invention. For example, a mixture of propylene glycol and dipropylene glycol can be utilized in the stick composition according to the present invention.

A necessary component of the cosmetic stick composition according to the present invention is a gel-forming agent. The gel forming agents used herein can be those utilized in U.S. Pat. No. 4,759,924, the contents of which have been previously incorporated herein by reference and include soaps of saturated and unsaturated fatty acids. These include, for example, the sodium salts (that is, soaps) of various fatty acids. Fatty acids which can be used for the gel forming agents include fatty acids having a carbon chain length of $C_{12}$–$C_{22}$ (including a mixture of different saturated fatty acids of carbon chain length in the range $C_{12}$–$C_{22}$).

Preferred gel-forming agents according to the present invention include soaps of relatively long-length carbon chain fatty acids (for example, carbon chain lengths of $C_{20}$–$C_{22}$). By utilizing such relatively long chain length fatty acids, a product is provided having a relatively high melting temperature, and, correspondingly, relatively greater stability.

A preferred gel-forming agent according to the present invention includes a mixture of sodium fatty acid soaps, having different fatty acid portions. For example, the soap gel-forming agent can be a mixture of sodium laurate, sodium myristate, sodium palmitate, sodium stearate, sodium arachidate, and sodium behenate, with the sodium fatty acid soaps respectively having the following distribution:

| Fatty Acid Soap | % (by weight, of the soap mixture) |
| --- | --- |
| Sodium laurate | 2% |
| Sodium myristate | 4–7% |
| Sodium palmitate | 35–44% |
| Sodium stearate | 31–44% |
| Sodium arachidate | 7–9% |
| Sodium behenate | 8–10% |

The mixture of sodium fatty acid soaps, having the desired distribution, can be provided in any number of ways known in the art. For example, pure sodium laurate, sodium myristate, etc., can be mixed together in desired proportions. Or different mixtures of sodium fatty acid soaps (for example, commercial grade sodium stearate, containing sodium stearate, sodium palmitate, etc., and another mixture of sodium fatty acid soaps) can be combined to provide the desired distribution.

The foregoing fatty acid soap distribution of the soap gel-forming agent is illustrative and not limiting of the present invention. Another mixture of sodium fatty acid soaps, having the following distribution, would also be appropriate for the present invention:

| Fatty Acid Soap | % (by weight, of the soap mixture) |
| --- | --- |
| Sodium laurate | 2% |
| Sodium myristate | 4–8% |
| Sodium palmitate | 30–39% |
| Sodium stearate | 29–43% |
| Sodium arachidate | 10–12% |
| Sodium behenate | 11–13% |

As described previously, the transparent, clear cosmetic stick composition according to the present invention should include an effective amount of the Eumulgin compound so as to provide a transparent, clear cosmetic stick composition and maintain such transparency and clarity. Illustratively, and not limiting, the composition can contain 1%–9% by weight of the Eumulgin compound. Illustratively, and not limiting, the cosmetic stick composition according to the present invention can also include the following amounts (in percent by weight of the total weight of the composition) of other components:

Alcohol (e.g., propylene glycol): 55–80%
Water: 9–25%
Soap: 4–10%

Note that as the amount of water included in the composition increases, the solidified composition has a tendency to become more hazy.

The compositions according to the present invention can include additional ingredients, beyond those previously described. For example, the following ingredients can optionally be included in the stick composition, although not necessary components according to the present invention: amino alkanols, such as amino methyl propanol, amino butanol and triethanol amine (this component helps in clarifying the composition); Poloxamines, such as Poloxamine 1307; sodium citrate; Poloxamers, such as Poloxamer 407; cocamide DEA; PPG-10 Cetyl Ether; PPG-8-Ceteth-20; dimethicone copolyol; sodium bicarbonate; butanol; cocoates; ethoxylated glycerin; Steareth-20; Isosteareth-20; and PPG-14 Butyl Ether. These ingredients can be included in the composition in amounts (e.g., up to 10% by weight of the total weight of the composition) so as not to disadvantageously effect the clarity and transparency of the stick composition.

Generally, other materials which can be included in the transparent, clear stick composition according to the present invention include polyols, fatty alcohols, alkanolamides, coloring agents, essential oils, and inorganic soluble salts of sodium or potassium.

The compositions according to the present invention also can include various cosmetic active ingredients. Thus, ingredients such as deodorants, sunscreens, skin conditioners, nail conditioners and the like can be included in the composition, provided they do not disadvantageously affect the clear and transparent final product and, e.g., can be applied to the human body. Various cosmetic active ingredients are described in U.S. Pat. No. 5,128,123, the contents of which are incorporated herein by reference in their entirety.

As indicated previously, compositions according to the present invention have use as deodorant compositions (e.g., by application to axillary regions of the human body), when having deodorant active materials incorporated therein. Various deodorant active materials which can be included in compositions according to the present invention are described in U.S. Pat. No. 4,759,924, and include bacteriostats and fragrances (e.g., perfumes), among others. For example, a deodorant material useful in the present compositions is 2-4-4'-trichloro-2'-hydroxydiphenyl ether (Triclosan).

Other ingredients such as dyes, pigments, coloring agents, etc., which do not disadvantageously affect the clarity and/or transparency of the solid stick compositions of the present invention, can be incorporated in the compositions.

The compositions according to the present invention are manufactured by processing techniques conventional in the art. Specifically, the solid components of the composition are melted and then the components are mixed. Preferably, the fragrance (if any) is added last, with the previously mixed components being cooled to a lower temperature (while still maintaining a liquid) prior to adding the fragrance. While still in the liquid state, the composition is filled in its package (e.g., at approximately 5° C. above titre) and then cooled to solidify the product in the package.

The compositions according to the present invention are utilized by conventional techniques. For example, when utilizing compositions according to the present invention as a deodorant solid stick, having deodorant active materials incorporated therein, the solid stick product is elevated out of the dispensing package so as to expose the stick, and the exposed portion of the stick is then rubbed against, e.g., the axillary region of the human body so as to deposit the deodorant active materials in the axillary region.

The following examples further describe and demonstrate embodiments within the scope of the present invention. The examples are given solely for the purpose of illustration and are not to be construed as limitations of the invention. Many variations thereof are possible without departing from the spirit and scope of the present invention.

In the following examples, the stated percentages are percentages by weight, of the stated component, of the total weight of the composition. The names utilized are the CTFA designations for the ingredients.

Also, in the following examples, soap gel-forming agents "A", "B" and "C" are referred to Each of these soap gel-forming agents is mixtures of different sodium fatty acid soaps, with different fatty acid portions, as set forth in the following:

| Soap Gel-Forming Agent A: | |
|---|---|
| Fatty Acid Soap | % (by weight, of the soap mixture) |
| Sodium laurate | 2% |
| Sodium myristate | 4–7% |
| Sodium palmitate | 35–44% |
| Sodium stearate | 31–44% |
| Sodium arachidate | 7–9% |
| Sodium behenate | 8–10% |

| Soap Gel-Forming Agent B: | |
|---|---|
| Fatty Acid Soap | % (by weight, of the soap mixture) |
| Sodium laurate | 2% |
| Sodium myristate | 4–8% |
| Sodium palmitate | 30–39% |
| Sodium stearate | 29–43% |
| Sodium arachidate | 10–12% |
| Sodium behenate | 11–13% |

| Soap Gel-Forming Agent C: | |
|---|---|
| Fatty Acid Soap | % (by weight, of the soap mixture) |
| Sodium laurate | 1% |
| Sodium myristate | 4–10% |
| Sodium palmitate | 20–30% |
| Sodium stearate | 25–42% |
| Sodium arachidate | 15–18% |
| Sodium behenate | 17–20% |

EXAMPLE I

| Ingredients | |
|---|---|
| Soap Gel-Forming Agent A | 5.00 |
| Propylene Glycol | 74.00 |
| Triclosan | 0.25 |
| Deionized Water | 11.56 |
| PPG-2-Ceteareth-9 | 3.00 |
| Poloxamer 407 | 5.00 |
| Fragrance | 1.00 |
| Color | 0.19 |

The composition of Example I was manufactured utilizing the following steps. Initially, the propylene glycol was heated to 88°±3° C. Thereafter, the Triclosan was added and mixed into the propylene glycol until dissolved. The soap gel-forming Agent A was then added, at 88°±3° C., and mixed into the propylene glycol/Triclosan mixture until dissolved. Thereafter, the PPG-2-Ceteareth-9 and Poloxamer 407 were added and mixed to be dissolved in the aforementioned mixture, at 88°±3° C. Then, the deionized water was added and mixed, the resulting mixture being cooled to 70°±2° C. Then, the color and fragrance were added. Thereafter, the resulting mixture was filled into solid stick packages, at approximately 5° C. above titre, and cooled in the package.

Given below is another example of the present invention.

EXAMPLE II

| Ingredients | |
|---|---|
| Soap Gel-Forming Agent A | 5.0 |
| Propylene Glycol | 74.00 |
| Triclosan | 0.25 |
| Deionized Water | 14.09 |
| PPG-2-Ceteareth-9 | 5.00 |
| Sodium Citrate | 0.50 |
| Fragrance | 1.00 |
| Color | 0.16 |

This composition of Example II was formed by the same processing steps as set forth in Example I, except that, prior to addition of the deionized water, sodium citrate was dissolved in the deionized water; thereafter, the deionized water/sodium citrate was mixed in the mixture of soap gel-forming agent A, propylene glycol, Triclosan, and PPG-2-Ceteareth-9 and the resulting mixture cooled to 70°±2° C.

The following Examples III–XIX illustratively define further clear, transparent solid cosmetic stick compositions according to the present invention.

EXAMPLE III

| Ingredients | |
|---|---|
| Sodium stearate | 5.00 |
| Propylene glycol | 73.29 |
| Triclosan | 0.25 |
| Deionized water | 14.56 |
| PPG-2-Ceteareth-9 | 5.5 |
| Color | 0.4 |
| Fragrance | 1.0 |

EXAMPLE IV

| Ingredients | |
|---|---|
| Sodium stearate | 4.00 |
| Propylene glycol | 73.00 |
| Triclosan | 0.25 |
| Deionized water | 14.85 |
| PPG-2-Ceteareth-9 | 5.5 |
| Aminomethyl propanol | 1.00 |
| Color | 0.4 |
| Fragrance | 1.00 |

EXAMPLE V

| Ingredients | |
|---|---|
| Sodium stearate | 4.00 |
| Propylene glycol | 73.59 |
| Triclosan | 0.25 |
| Deionized water | 14.56 |
| PPG-2-Ceteareth-9 | 5.5 |
| Sodium chloride | 0.5 |
| Stearyl alcohol | 0.2 |
| Color | 0.4 |
| Fragrance | 1.00 |

EXAMPLE VI

| Ingredients | |
|---|---|
| Soap Gel-Forming Agent A | 5.0 |
| Propylene glycol | 74.0 |
| Triclosan | 0.25 |
| Deionized water | 18.56 |
| PPG-2-Ceteareth-9 | 1.00 |
| Color | 0.19 |

EXAMPLE VII

| Ingredients | |
|---|---|
| Soap Gel-Forming Agent A | 5.0 |
| Propylene glycol | 74.0 |
| Triclosan | 0.25 |
| Deionized water | 13.56 |
| PPG-2-Ceteareth-9 | 5.0 |
| N,N,N',N',-tetrakis(2-hydroxypropyl) ethylenediamine | 1.0 |
| Color | 0.19 |
| Fragrance | 1.0 |

EXAMPLE VIII

| Ingredients | |
|---|---|
| Soap Gel-Forming Agent A | 5.0 |
| Propylene glycol | 74.0 |
| Triclosan | 0.25 |
| Deionized water | 14.56 |
| PPG-2-Ceteareth-9 | 3.0 |
| PPG-5-Ceteth-20 | 2.0 |
| Color | 0.19 |
| Fragrance | 1.0 |

EXAMPLE IX

| Ingredients | |
|---|---|
| Soap Gel-Forming Agent A | 5.0 |
| Propylene glycol | 74.0 |
| Triclosan | 0.25 |
| Deionized water | 14.56 |
| PPG-2-Ceteareth-9 | 3.0 |
| PPG-10 Cetyl Ether | 2.0 |
| Color | 0.19 |
| Fragrance | 1.00 |

EXAMPLE X

| Ingredients | |
|---|---|
| Soap Gel-Forming Agent A | 5.0 |
| Propylene glycol | 74.0 |
| Triclosan | 0.25 |
| Deionized water | 14.56 |
| PPG-2-Ceteareth-9 | 2.0 |
| PPG-3 Myristyl Ether | 3.0 |
| Color | 0.19 |
| Fragrance | 1.0 |

EXAMPLE XI

| Ingredients | |
|---|---|
| Soap Gel-Forming Agent A | 5.0 |
| Propylene glycol | 66.00 |
| Triclosan | 0.25 |
| Deionized water | 14.59 |
| PPG-2-Ceteareth-9 | 3.00 |
| PPG-14 Butyl Ether | 10.00 |
| Color | 0.16 |
| Fragrance | 1.00 |

EXAMPLE XII

| Ingredients | |
|---|---|
| Soap Gel-Forming Agent A | 5.0 |
| Propylene glycol | 18.5 |
| Dipropylene glycol | 55.5 |
| Triclosan | 0.25 |
| Deionized water | 16.72 |
| PPG-2-Ceteareth-9 | 3.00 |
| Color | 0.03 |
| Fragrance | 1.00 |

EXAMPLE XIII

| Ingredients | |
|---|---|
| Soap Gel-Forming Agent A | 5.0 |
| Propylene glycol | 74.00 |
| Triclosan | 0.25 |
| Deionized water | 14.09 |
| PPG-2-Ceteareth-9 | 5.00 |
| Sodium citrate | 0.50 |
| Color | 0.16 |
| Fragrance | 1.00 |

EXAMPLE XIV

| Ingredients | |
|---|---|
| Soap Gel-Forming Agent C | 6.00 |
| Propylene glycol | 70.25 |
| Triclosan | 0.25 |
| Deionized water | 17.31 |
| PPG-2-Ceteareth-9 | 3.00 |
| Cocamide DEA | 2.00 |
| Color | 0.19 |
| Fragrance | 1.0 |

EXAMPLE XV

| Ingredients | |
|---|---|
| Soap Gel-Forming Agent C | 4.50 |
| Propylene glycol | 74.00 |
| Triclosan | 0.25 |
| Deionized water | 13.86 |
| PPG-2-Ceteareth-9 | 5.00 |
| Sodium chloride | 1.00 |
| Stearyl alcohol | 0.20 |
| Color | 0.19 |
| Fragrance | 1.00 |

EXAMPLE XVI

| Ingredients | |
|---|---|
| Soap Gel-Forming Agent A | 6.00 |
| Propylene glycol | 74.00 |
| Triclosan | 0.25 |
| Deionized water | 13.56 |
| PPG-2-Ceteareth-9 | 4.00 |
| Sodium bicarbonate | 1.0 |
| Color | 0.19 |
| Fragrance | 1.00 |

EXAMPLE XVII

| Ingredients | |
| --- | --- |
| Soap Gel-Forming Agent B | 6.00 |
| Propylene glycol | 73.51 |
| Triclosan | 0.25 |
| Deionized water | 14.80 |
| PPG-2-Ceteareth-9 | 3.00 |
| Stearyl alcohol | 0.25 |
| Triethanolamine | 1.00 |
| Color | 0.19 |
| Fragrance | 1.00 |

EXAMPLE XVIII

| Ingredients | |
| --- | --- |
| Soap Gel-Forming Agent A | 7.0 |
| Propylene glycol | 69.00 |
| Triclosan | 0.25 |
| Deionized water | 14.56 |
| PPG-2-Ceteareth-9 | 4.00 |
| 2-amino-1-butanol | 1.00 |
| Isosteareth-20 | 3.0 |
| Color | 0.19 |
| Fragrance | 1.0 |

EXAMPLE XIX

| Ingredients | |
| --- | --- |
| Sodium stearate | 5.0 |
| Propylene glycol | 71.79 |
| Triclosan | 0.25 |
| Deionized water | 14.56 |
| PPG-2-Ceteareth-9 | 7.0 |
| Fragrance | 1.00 |
| Color | 0.4 |

While we have shown and described several embodiments in accordance with the present invention, it is understood that the same is not limited thereto, but is susceptible of numerous changes and modifications as known to those skilled in the art. Therefore, we do not wish to be limited to the details shown and described herein, but intend to cover all such changes and modifications as are encompassed by the scope of the appended claims, including equivalents thereof.

The following U.S. patent application, filed concurrently herewith, the contents of which are incorporated herein by reference in their entirety, contains subject matter related to the subject matter of the present application:

Bhalchandra D. Moghe and Radhakrishna B. Kasat, "Transparent Clear Cosmetic Stick Composition Containing Sodium Salts of Methyl Carboxyl Derivatives of EthoxylatedLauryl Alcohol" (Attorney Docket No. 851.31663X00).

We claim:

1. A transparent, clear stick composition consisting essentially of an alcohol and water, and gelled with at least one alkali metal salt of a fatty acid, the fatty acid component of the at least one alkali metal salt having a carbon chain length in a range of $C_{12}$–$C_{22}$, with at least some of the fatty acid component being at least one of $C_{20}$ fatty acid and $C_{22}$ fatty acid, the composition also containing an Eumulgin compound, in an effective amount to provide a transparent, clear stick composition, and optionally being present at least one material selected from the group consisting of a sodium chloride, stearyl alcohol and deodorant active ingredients, the composition consisting essentially of the alcohol, water, alkali metal salt of a fatty acid, Eumulgin compound and, where present, said at least one material.

2. The composition as defined in claim 1, wherein sodium chloride and stearyl alcohol are present.

3. The composition as defined in claim 2, wherein the sodium chloride is present in the composition in an amount up to 1% by weight, and the stearyl alcohol is present in the composition in an amount up to 0.5% by weight, of the total weight of the composition.

4. The composition as defined in claim 2, wherein deodorant active materials are present, whereby the composition is a transparent deodorant stick composition.

5. The composition as defined in claim 1, wherein the Eumulgin compound is Ceteareth-30.

6. The composition as defined in claim 5, wherein deodorant active materials are present, whereby the composition is a transparent deodorant stick composition.

7. The composition as defined in claim 1, wherein the alcohol includes propylene glycol.

8. The composition as defined in claim 7, wherein said Eumulgin compound is PPG-2-Ceteareth-9.

9. The composition as defined in claim 8, wherein the at least one alkali metal salt of a fatty acid is at least one sodium salt of a fatty acid, the fatty acid component having a carbon chain length in the range of $C_{12}$ to $C_{22}$, with at least some of the fatty acid component being at least one of $C_{20}$ fatty acid and $C_{22}$ fatty acid.

10. The composition as defined in claim 9, wherein the PPG-2-Ceteareth-9 is included in the composition in an amount of 1%–9% by weight of the total weight of the composition.

11. The composition as defined in claim 10, wherein sodium chloride and stearyl alcohol are present.

12. The composition as defined in claim 11, wherein deodorant active materials are present, whereby the composition is a transparent deodorant stick composition.

13. The composition as defined in claim 1, wherein the at least one alkali metal salt of a fatty acid includes sodium arachidate and sodium behenate, respectively in amounts in the range of 7%–18%, and 8%–20% by weight, of the total weight of alkali metal salt of a fatty acid in the composition.

14. The composition as defined in claim 1, wherein the at least one alkali metal salt of a fatty acid is a mixture of sodium laurate, sodium myristate, sodium palmitate, sodium stearate, sodium arachidate and sodium behenate.

15. The composition as defined in claim 14, wherein the mixture includes 1%–2% by weight sodium laurate, 4%–10% by weight sodium myristate, 20%–44% by weight sodium palmitate, 25%–44% by weight sodium stearate, 7%–18% by weight sodium arachidate and 8%–20% by weight sodium behenate, of the total weight of the mixture.

16. The composition as defined in claim 1, consisting of said alcohol, water, said at least one alkali metal salt of a fatty acid, said Eumulgin compound and, where present, said at least one material.

17. A transparent, clear stick composition consisting essentially of an alcohol and water, and gelled with at least one alkali metal salt of a fatty acid, the fatty acid component of the at least one alkali metal salt having a carbon chain length in a range of $C_{12}$–$C_{22}$, with at least some of the fatty acid component being at least one of $C_{20}$ fatty acid and $C_{22}$ fatty acid, the composition also containing an Eumulgin compound, in an effective amount to provide a transparent, clear stick composition, the composition consisting essentially of said alcohol, water, said at least one alkali metal salt and said Eumulgin compound.

18. The composition as defined in claim 17, wherein said Eumulgin compound is PPG-2-Ceteareth-9.

19. The composition as defined in claim 18, wherein the at least one alkali metal salt of a fatty acid is at least one sodium salt of a fatty acid, the fatty acid component having a carbon chain length of $C_{12}$ to $C_{22}$, with at least some of the fatty acid component being at least one of $C_{20}$ fatty acid and $C_{22}$ fatty acid.

20. The composition as defined in claim 19, wherein the at least one sodium salt of a fatty acid is mixture of sodium salts of fatty acids having carbon chain lengths in the range of $C_{12}$ to $C_{22}$, with at least some of the fatty acid component being at least one of $C_{20}$ fatty acid and $C_{22}$ fatty acid.

21. The composition as defined in claim 18, wherein the PPG-2-Ceteareth-9 is included in the composition in an amount of 1%–9% by weight of the total weight of the composition.

22. The composition as defined in claim 17, wherein the alcohol includes polyhydric alcohols.

23. The composition as defined in claim 22, wherein the polyhydric alcohols include a mixture of polyhydric alcohols.

24. The composition as defined in claim 23, wherein the mixture of polyhydric alcohols includes propylene glycol and dipropylene glycol.

25. The composition as defined in claim 24, wherein said Eumulgin compound is PPG-2-Ceteareth-9.

26. The composition as defined in claim 24, wherein the Eumulgin compound is Ceteareth-30.

27. The composition as defined in claim 17, wherein the alcohol includes monohydric alcohols.

28. The composition as defined in claim 27, wherein said Eumulgin compound is PPG-2-Ceteareth-9.

29. The composition as defined in claim 27, wherein the Eumulgin compound is Ceteareth-30.

30. The composition as defined in claim 17, wherein the at least one alkali metal salt of a fatty acid includes sodium arachidate and sodium behenate, respectively in amounts in the range of 7%–18%, and 8%–20% by weight, of the total weight of alkali metal salt of a fatty acid in the composition.

31. The composition as defined in claim 17, wherein the at least one alkali metal salt of a fatty acid is a mixture of sodium laurate, sodium myristate, sodium palmitate, sodium stearate, sodium arachidate and sodium behenate.

32. The composition as defined in claim 31, wherein the mixture includes 1%–2% by weight sodium laurate, 4%–10% by weight sodium myristate, 20%–44% by weight sodium palmitate, 25%–44% by weight sodium stearate, 7%–18% by weight sodium arachidate and 8%–20% by weight sodium behenate of the total weight of the mixture.

33. A transparent, clear stick composition base for a transparent, clear cosmetic stick composition, whereby a cosmetically active ingredient can be incorporated in the composition base to provide the transparent, clear cosmetic stick composition, the stick composition base consisting essentially of an alcohol and water, and gelled with at least one alkali metal salt of a fatty acid, the fatty acid component of the at least one alkali metal salt having a carbon chain length in a range of $C_{12}$–$C_{22}$, with at least some of the fatty acid component being at least one of $C_{20}$ fatty acid and $C_{22}$ fatty acid, the stick composition base also containing an Eumulgin compound, in an effective amount to provide a transparent, clear cosmetic stick composition, and optionally containing at least one of sodium chloride and stearyl alcohol, the stick composition base consisting essentially of the alcohol, water, alkali metal salt of a fatty acid and Eumulgin compound, and, where present, said at least one of sodium chloride and stearyl alcohol.

34. A transparent, clear deodorant stick composition consisting essentially of the stick composition base of claim 33 and at least one deodorant active material.

35. The stick composition base as defined in claim 33, consisting of the alcohol, water, alkali metal salt of a fatty acid and Eumulgin compound, and, where present, said at least one of sodium chloride and stearyl alcohol.

* * * * *